United States Patent
Langlois

(10) Patent No.: US 11,076,843 B2
(45) Date of Patent: Aug. 3, 2021

(54) ORGAN RETENTION DEVICE AND SYSTEM, AND USE OF SAME FOR LAPAROSCOPIC SURGERY

(71) Applicant: Mariner Endosurgery Inc., Hamilton (CA)

(72) Inventor: David Allan Langlois, Burlington (CA)

(73) Assignee: MARINER ENDOSURGERY INC., Hamilton (CA)

( * ) Notice: Subject to any disclaimer, the term of this patent is extended or adjusted under 35 U.S.C. 154(b) by 0 days.

(21) Appl. No.: 16/248,164

(22) Filed: Jan. 15, 2019

(65) Prior Publication Data

US 2019/0231336 A1   Aug. 1, 2019

Related U.S. Application Data

(60) Provisional application No. 62/617,503, filed on Jan. 15, 2018.

(51) Int. Cl.
*A61B 17/02* (2006.01)
*A61B 90/90* (2016.01)
*A61B 17/42* (2006.01)
*A61B 90/30* (2016.01)
(Continued)

(52) U.S. Cl.
CPC ...... *A61B 17/0218* (2013.01); *A61B 17/0483* (2013.01); *A61B 17/4241* (2013.01);
(Continued)

(58) Field of Classification Search
CPC ......... A61B 17/0218; A61B 2017/0225; A61F 2250/0096; A61F 2250/0097; A61F 2250/0098
(Continued)

(56) References Cited

U.S. PATENT DOCUMENTS 3,187,752 A * 6/1965 Glick ............... A61L 17/145
                                                606/231
5,405,360 A * 4/1995 Tovey ............... A61F 2/0063
                                                606/151
(Continued)

FOREIGN PATENT DOCUMENTS

WO    2003/096907 A1    11/2003
WO    2012/087112 A1    6/2012

OTHER PUBLICATIONS

Extended European Search Report for EP Patent Application No. 19151762 dated May 17, 2019.
(Continued)

*Primary Examiner* — Matthew J Lawson
*Assistant Examiner* — Lisa Nguyen
(74) *Attorney, Agent, or Firm* — Millman IP Inc.

(57) ABSTRACT

An organ retention device and system, and use of the same for laparoscopic surgery is provided. The organ retention device includes a biologically compatible flexible barrier configured to restrain one or more organs. First and second anchor strings extend from first and second connection regions of the flexible barrier respectively and have a first and a second loop distal from the flexible barrier. At least one expansion element is configured to expand the flexible barrier generally perpendicularly to an axis between the first connection region and the second connection region when the first loop and the second loop are held apart in tension. A retraction device is also provided having a sharp distal end configured to enter an abdominal cavity by puncturing the abdominal wall, and a hook proximate to the sharp distal end configured to catch and retract one of the loops.

17 Claims, 7 Drawing Sheets

(51) Int. Cl.
    *A61B 34/20* (2016.01)
    *A61B 17/06* (2006.01)
    *A61B 17/04* (2006.01)
    *A61B 90/94* (2016.01)
    *A61B 90/00* (2016.01)
(52) U.S. Cl.
    CPC ....... *A61B 90/94* (2016.02); *A61B 2017/0225* (2013.01); *A61B 2017/06042* (2013.01); *A61B 2034/2057* (2016.02); *A61B 2034/2065* (2016.02); *A61B 2090/3612* (2016.02); *A61B 2090/3937* (2016.02)
(58) Field of Classification Search
    USPC ................. 600/204, 205, 206, 207, 208; 623/1.11–1.54
    See application file for complete search history.

(56) References Cited

U.S. PATENT DOCUMENTS

| | | | | |
|---|---|---|---|---|
| 6,251,135 B1* | 6/2001 | Stinson | ............... | A61F 2/82 623/1.34 |
| 2002/0082683 A1* | 6/2002 | Stinson | ............... | A61F 2/90 623/1.23 |
| 2008/0146881 A1* | 6/2008 | Alimi | ............... | A61B 17/0218 600/204 |
| 2009/0062618 A1* | 3/2009 | Drew | ............... | A61B 17/0218 600/204 |
| 2009/0137877 A1* | 5/2009 | Minnelli | ............... | A61B 17/0218 600/204 |
| 2010/0081880 A1* | 4/2010 | Widenhouse | ............... | A61B 17/3423 600/201 |
| 2012/0253111 A1* | 10/2012 | Ahluwalia | ............... | A61B 17/0218 600/37 |
| 2014/0194926 A1* | 7/2014 | Bailly | ............... | A61F 2/0063 606/213 |
| 2018/0008254 A1* | 1/2018 | Ahluwalia | ............... | A61B 17/0218 |
| 2019/0133566 A1* | 5/2019 | Pettus, IV | ............... | A61B 17/3423 |

OTHER PUBLICATIONS

Communication pursuant to Article 94(3) EPC for EP application No. 19151762.2, dated Nov. 25, 2020.

* cited by examiner

ORGAN RETENTION DEVICE AND SYSTEM, AND USE OF SAME FOR LAPAROSCOPIC SURGERY

CROSS-REFERENCE TO RELATED APPLICATIONS

This application claims the benefit of U.S. Provisional Application No. 62/617,503, filed Jan. 15, 2018, the contents of which are incorporated herein by reference in their entirety.

FIELD

The present invention relates to systems for reducing accidental injury to patients during surgery and more particularly to an organ retention device and system, and use of the same, for laparoscopic surgery.

BACKGROUND OF THE DISCLOSURE

Compared with conventional surgery, laparoscopic surgery is an excellent means for achieving significant reductions in surgery-related morbidity. These reductions are achieved, however, only if the procedure is performed completely and without effective errors. Unfortunately, error-free laparoscopic surgeries are not the rule. Indeed, intra-operative and post-operative complications are all too common with laparoscopic surgery procedures. Because of this, there is a need to improve patient safety during laparoscopic surgery so that the benefits derived from such procedures are achieved while the drawbacks are reduced or eliminated.

One of the most profound drawbacks of laparoscopic surgery is the occurrence of unintentional or inadvertent injuries to patient tissue structures adjacent to or sometimes, distant from the intended surgical site or field. In the pelvic cavity, for example, bowels, ureters, large organs and blood vessels can be injured either directly from the heat or sharpness of the laparoscopic instruments, or burned indirectly through the conduction of heat through nearby tissues. Typically, such injuries are not appreciated at the time of surgery because the specific injury sites are hidden by blood or other patient tissues. As another disadvantage attendant to such iatrogenic injuries, the response to the unintended injury manifested by the patient is often a delayed one. This delayed response can be traumatic as well as tragic, and can sometimes result in one or more further surgeries, which would otherwise be unnecessary.

The implications from both a medical perspective as well as a medico-legal perspective are enormous. Obviously, such injuries are negative events and therefore best avoided. The present invention is therefore directed to reducing the occurrence and severity of these negative events. The proposed invention that is insertable into the body of the patient is positionable to restrain at least of the internal body portions of the patient from obstructing the surgical instrument.

U.S. Pat. No. 9,247,932 describes a retraction system comprising a retraction fiber control part that is passed through the trocar port of the body. However, this device relies upon the retraction fibers being held between two trocar sheathes, taking up two valuable ports for tool insertion and movement, which would likely prove frustrating to surgeons from a workflow optimization perspective, and would likely necessitate the creation of additional incisions in the body. The ability to retract organs without taking up a valuable entry port is necessary for ensuring the surgical team is not encumbered with any blocked ports during surgery.

U.S. Pat. No. 8,852,088 attempts to resolve the workflow issue by describing a surgical retraction device that preserves trocars upon deployment of the system. By introducing an anchor that is selectively deployable to a tissue not to be retracted and then an extendable grasper that can be deployed to a tissue desired to be retracted, the proposed invention eliminates the dependency upon two trocars. In an example use, the grasper piece can clutch a gall bladder, and the anchor can be affixed to the abdominal wall, with the tether line connecting the grasping point, to the anchor point and out through the trocar. Pulling back on the tether creates a lever that pulls the gall bladder upwards, as well as the liver, which sits above the gall bladder. However, the tether line still runs out the trocar, which does not allow for full freedom of movement of additional surgical tools presented through the trocar port. Another disadvantage of U.S. Pat. No. 8,852,088 is the ability to only retract one tissue at a time. In laparoscopic surgeries in the lower abdomen, and in particular bariatric patients, multiple organs can be deforming and moving simultaneously.

Both U.S. Pat. Nos. 9,247,932 and 8,852,088 attempt to resolve keeping trocars available, while removing the need for a physician's assistant to physically hold a retractor fan or lifter. However, for an organ retention device to maximize utility in an operating room, it must retract organs without any reliance or anchoring upon trocar parts, and must be capable of restraining multiple organs simultaneously. These factors are critical for surgeons to attend to the surgical site without delay or occlusion of the field of view.

SUMMARY OF THE DISCLOSURE

In one aspect, there is provided an organ retention device, comprising a biologically compatible flexible barrier configured to restrain one or more organs, a first anchor string extending from a first connection region of the flexible barrier, a second anchor string extending from a second connection region of the flexible barrier, and at least one expansion element coupled to the flexible barrier at a region spaced from an axis between the connection regions when the first connection region and the second connection region are held apart in tension and configured to expand the flexible barrier generally perpendicularly to the axis.

The flexible barrier can comprise a netting.

The first anchor string can have a first loop distal from the flexible barrier and the second anchor string can have a second loop distal from the flexible barrier.

The at least one expansion element can comprise supplementary weighting along a weighted peripheral region of the flexible barrier spaced from the axis between the first connection region and the second connection region, the supplementary weighting configured to cause the weighted peripheral region to hang down from the axis between the first connection region and the second connection region when the first connection region and the second connection region are held apart in tension.

The supplementary weighting can comprise material secured to the weighted peripheral region.

The weighting material can comprise silicone, and, in particular, silicone beading secured along the weighted peripheral region of the flexible barrier.

The organ retention device can further comprise a stiffening structure of the flexible barrier reducing the flexibility of the netting. The stiffening structure can comprise silicone beading secured to the netting. The silicone beading can be applied along a line that is generally non-parallel to the axis between the first connection region and the second connection region when the first connection region and the second connection region are held apart in tension.

The at least one expansion element can comprise a third anchor string extending from a third connection region of the flexible barrier, and a fourth anchor string extending from a fourth connection region of the flexible barrier.

The organ retention device can further comprise a fifth anchor string extending from a fifth connection region of the flexible barrier, the fifth connection region being positioned within a central region of the flexible barrier delimited by the first, second, third, and fourth connection regions. The third anchor string can have a third loop distal from the flexible barrier, the fourth anchor string can have a fourth loop distal from the flexible barrier, and the fifth anchor string can have a fifth loop distal from the flexible barrier.

The flexible barrier can be generally rectangular, and each of the first, second, third, and fourth connection regions can be proximate to a separate vertex of the flexible barrier.

The organ retention device can further comprise marking on the netting indicating orientation. The marking can comprise silicone beading on the netting.

In another aspect, there is provided the use of an organ retention device defined above.

In a further aspect, there is provided an organ retention system for laparoscopic surgery, comprising an organ retention device comprising a biologically compatible netting configured to restrain one or more organs, a first anchor string extending from a first connection region of the netting and having a first loop distal from the flexible barrier, a second anchor string extending from a second connection region of the netting and having a second loop distal from the flexible barrier, and at least one expansion element coupled to the netting at a region spaced from an axis between the connection regions when the first connection region and the second connection region are held apart in tension and configured to expand the netting generally perpendicularly to the axis, and an anchor string retraction device having a sharp distal end configured to enter an abdominal cavity by puncturing the abdominal wall of a patient, and a hook proximate to the sharp distal end configured to catch one of the loops of the organ retention device and retract the captured loop through viscera of the abdominal wall to anchor the corresponding connection region of the netting.

In still another aspect, there is provided a use of an organ retention system as defined immediately above.

BRIEF DESCRIPTIONS OF THE DRAWINGS

For a better understanding of the various embodiments described herein and to show more clearly how they may be carried into effect, reference will now be made, by way of example only, to the accompanying drawings in which.

DETAILED DESCRIPTION

Figure 1:
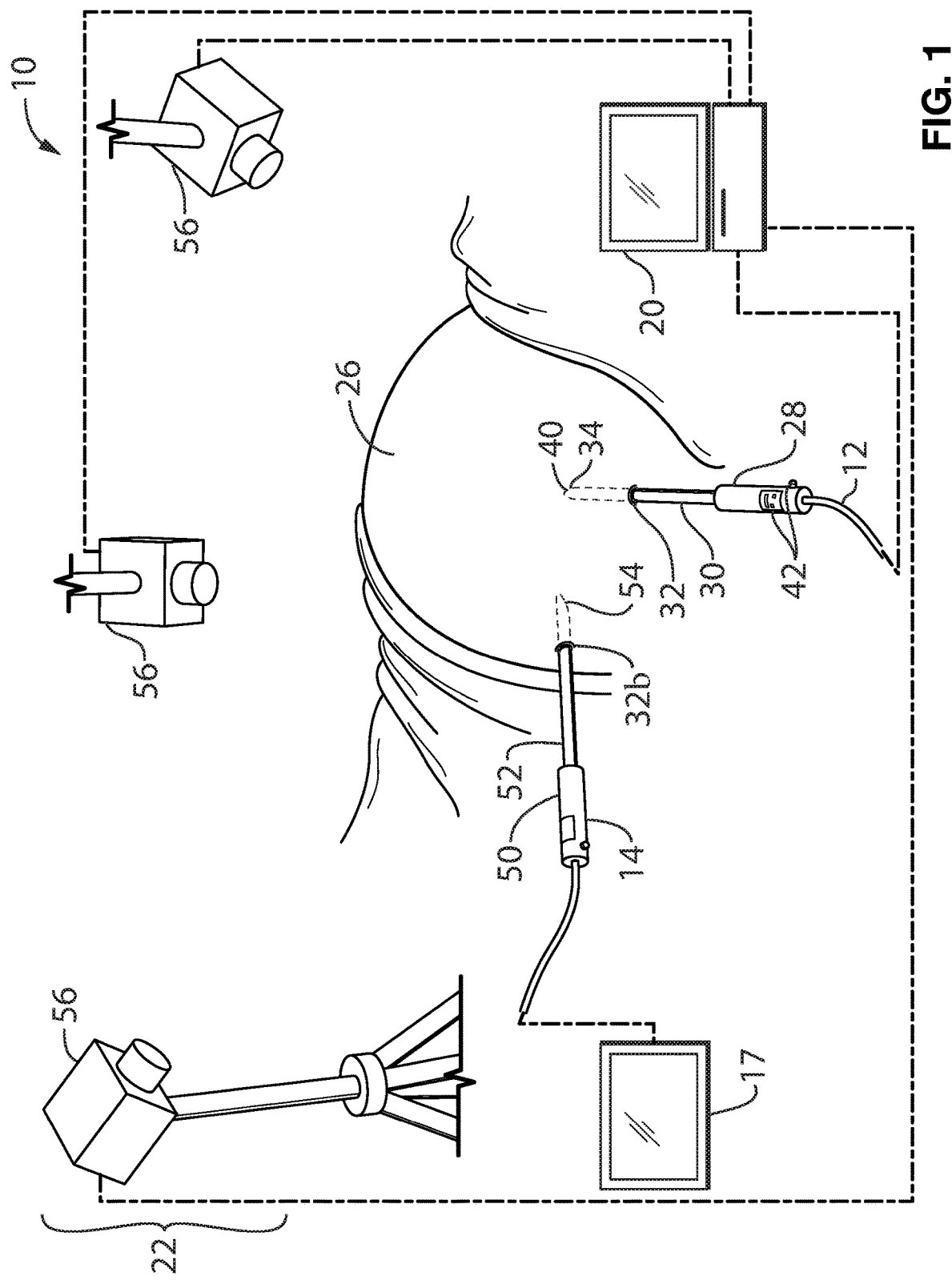
FIG. 1 illustrates is a top perspective view of a surgical system for use on the body of a patient in accordance with an embodiment of the present invention.

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

A device that aids in the retention of organs during laparoscopic surgery is disclosed herein as part of a surgery system. The device is intended for insertion into the abdominal cavity of the body to restrict the complicated, unpredictable movement of organs during surgery. The device includes a biologically compatible flexible barrier, such as a netting, that is configured to restrain one or more organs. First and second anchor strings extend from connection regions of the flexible barrier, each having a loop distal from the flexible barrier. The device includes at least one expansion element coupled to the flexible barrier at a region spaced from an axis between the connection regions when the first connection region and the second connection region are held apart in tension and configured to expand the flexible barrier generally perpendicularly to the axis. In some embodiments, the expansion element includes supplemental weighting along a weighted peripheral region of the flexible barrier distal to the connection regions. The weighting is configured to weigh the weighted peripheral region to hang down from the axis between the connection regions.

The device is tightly furled and passed through a port, unfurled within the body, and maneuvered and stretched across the organs by retracting the loops of the anchor strings via a retraction device such as a needle hook through the tissue of a patient to pull into place. After the flexible barrier is secured in place, the retraction device is removed. Upon completion of the surgery, the loops are cut and the flexible barrier is passed through the port used for entry. Organs that can require retention and/or retraction can include, but are not limited to, small bowels, large bowel, sigmoidal bowel, the liver, the gall bladder, the kidneys, the uterus, the stomach and other viscera typically found in the abdominal cavity. Described herein are only a few exemplary embodiments. One familiar with the art will recognize that parameters, including size and shape of the components of this invention, as well as the types of materials used for the components, may be altered to accommodate different types and/or sizes of organs and patient anatomy requiring retraction while staying within the scope of the invention described herein.

The organ retention device and methods described here utilize a system comprising, in combination, a biologically compatible flexible barrier, such as a mesh netting, and a delivery device for delivering the flexible barrier to the retention site, and allowing the flexible barrier to be unfurled and held in place against desired organs.

Figure 2:
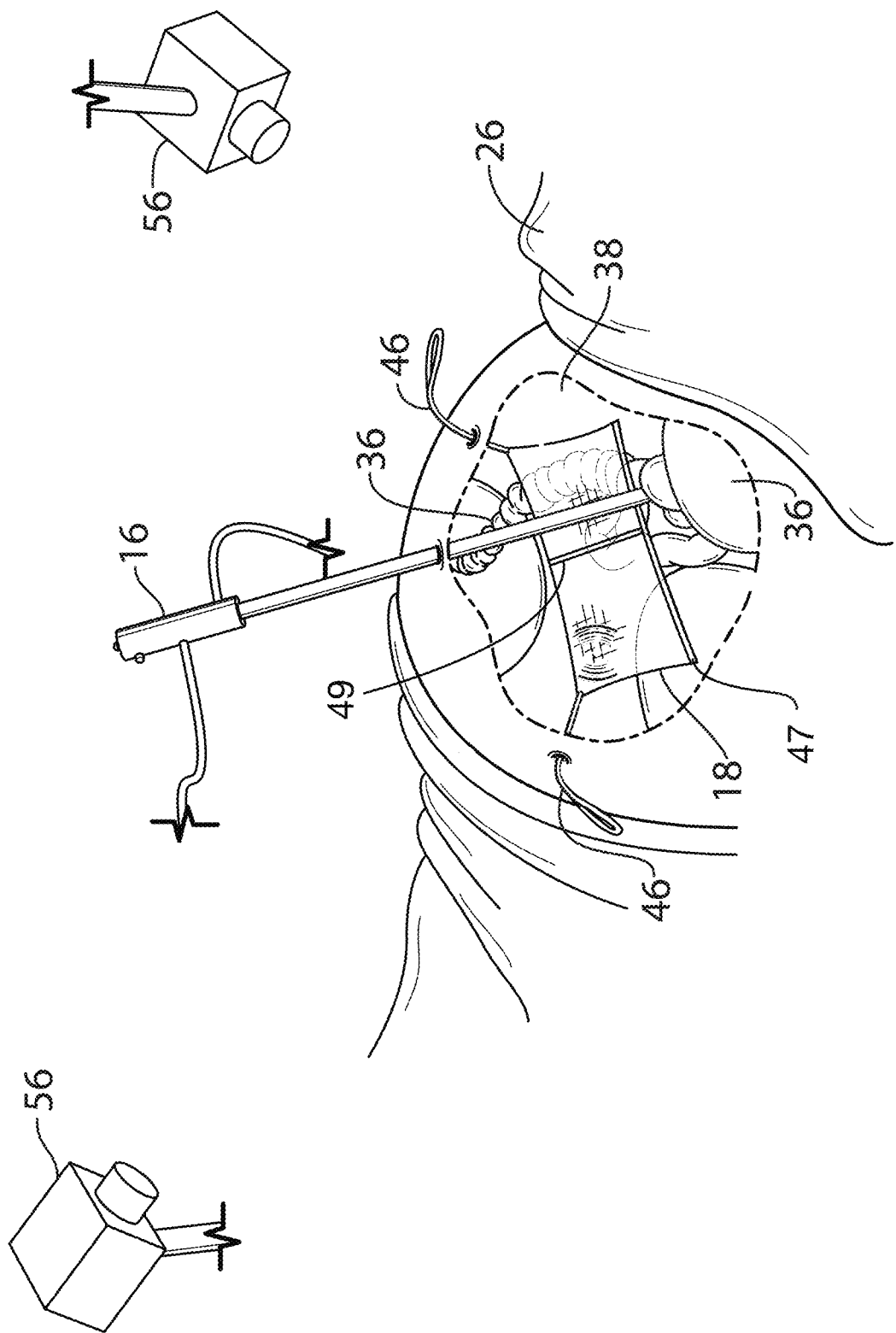
FIG. 2 illustrates the surgical system for use on the body of a patient of FIG. 1 with a portion of the body cut away.

Reference is made to FIGS. 1 and 2 which shows a surgical system 10 for use on a body of a patient in accordance with an embodiment of the invention. The surgical system 10 includes a probe 12, a laparoscope 14, a surgical instrument 16, a display 17, an organ retention device 18, a controller 20 and a tracking system 22, which in the embodiment shown is a camera system. The surgical system 10 is configured to reduce the incidence of injuries to patients during laparoscopic surgery.

The system 10 is initially used to determine a safe zone within the patient shown at 26 (only a portion of the patient 26 is shown in FIG. 1) in which the surgical instrument 16 can be maneuvered without causing injury to the patient 26. The determination of the safe zone involves the probe 12, the laparoscope 14 in particular. The probe 12 includes a probe body 28 and an interior portion 30 connected to the probe body 28. The interior portion 30 is configured to be at least partially inserted into the body of the patient 26 through one of a plurality of apertures 32 made in the body of the patient 26. The interior portion 30 is therefore made from a material that will not cause harm to the patient, such as, for example, a suitable stainless steel. The probe body 28 is configured to be outside the body of the patient 26 during use.

The probe 12 further includes a probing portion 34 on the interior portion 30. The probing portion 34 is a portion of the interior portion 30 and is used to identify the positions of points on the internal body portions shown at 36 (FIG. 2) of the patient 26 that are in the surgical field (i.e., that are in the vicinity of the particular site in the patient 26 that requires surgery). The surgical field is shown in FIG. 2 at 38. The probing portion 34 may be at a tip 40 of the interior portion 30.

During use of the probe 12, it is desired for a controller 20 to be able to determine the position of the probing portion 34 at selected times. To this end, a probe marker 42 is provided on the probe body 28. The probe marker 42 is, during use, viewed by the camera system 22 and is used by the controller 20 to identify the probe 12 (i.e., to distinguish the probe 12 over other objects, such as the instrument 16). Additionally or alternatively, the probe marker 42 is configured to provide sufficient information to the controller 20 for the controller 20 to be able to determine the position and orientation of the probe marker 42. By determining the position and orientation of the probe marker 42, the controller 20 can determine the position and orientation of the probe 12 itself and therefore can determine the position of the probing portion 34. Determining the position of the probing portion 34 is used by the controller 20 in determining where the internal body portions 36 of the patient 26 are, which is then used by the controller 20 to determine the safe zone 24.

The laparoscope 14 includes a laparoscope body 50 and an interior portion 52 connected to the laparoscope body 50. The interior portion 52 is configured to be at least partially inserted into the body of the patient 26 through one of the apertures 32. The particular aperture 32 through which the probe 12 is inserted is shown at 32b. The interior portion 52 is therefore made from a material that will not cause harm to the patient, such as, for example, a suitable stainless steel. The laparoscope body 50 is configured to be outside the body of the patient 26 during use.

The interior portion 52 includes an image receiving element. During use, the image receiving element is positionable in the surgical field 38 in the body of the patient 26 to receive images of the probing portion 34 when the image receiving element 54 is in the surgical field 38. The image receiving element 54 may be a lens, for example. The laparoscope 14 is configured by any suitable means to transmit received images to the display 17. For example, the laparoscope 14 may include an image sensor (not shown), which may be, for example, a CCD sensor or a CMOS sensor, that is positioned to receive images from the image receiving element 54. The laparoscope 14 is configured to transmit the images of the probing portion 34 to the display 17 (optionally via a controller such as the controller 20).

The surgical instrument 16 includes an instrument body and an interior portion connected to the instrument body. The interior portion is configured to be at least partially inserted into the body of the patient 26 during use. The instrument body is configured to be outside the body of the patient during use. The interior portion includes a functional element, which is an element that is configured to perform a particular function on the patient. For example, the functional element may be a cutting blade, a scissors mechanism or for example a heating element to cauterize. As will be understood, the functional element may cause unintended injury to the patient 26 if it is accidentally brought into contact with the internal body portions 36 of the patient 26 surrounding the surgical field 38.

During use of the surgical instrument 16, it is desired for the controller 20 to be able to determine the position of a functional element at the tip of the surgical instrument 16 substantially continuously. To this end, an instrument marker is provided on the instrument body. The instrument marker is, during use, viewed by the camera system 22 and may be used by the controller 20 to identify the surgical instrument 16 (i.e., to distinguish the surgical instrument 16 over other objects, such as the probe 12). Additionally or alternatively, the instrument marker is configured to provide sufficient information to the controller 20 for the controller 20 to be able to determine the position and orientation of the instrument 16. By determining the position and orientation of the instrument marker, the controller 20 can determine the position and orientation of the surgical instrument 16 itself and therefore can determine the position of the functional element. Determining the position of the functional element is used by the controller 20 in determining whether the functional element is within a safe zone 24.

The camera system 22 includes at least one camera 56 and preferably includes a plurality of cameras 56 mounted around the surgical theatre. The cameras 56 are positioned at selected positions to reduce the likelihood of obstruction of their view of the probe marker 42 and the instrument marker 96. The cameras 56 receive images of the probe marker 42 and transmit the images to the controller 20. The controller 20 is programmed to locate the probe marker 42 in the images and to determine by any suitable means, the position and orientation of the probe 12 and therefore the position of the probing portion 34. This may be achieved by comparing the images from two or more cameras 56 and using triangulation. Alternatively, a stereoscopic camera 56 may be used, so as to provide three-dimensional position information through images sent to the controller 20 without using multiple cameras. Alternatively, a single non-stereoscopic camera 56 may be used which sends a non-stereoscopic image to the controller 20. The controller 20 can determine easily the position of the marker 42 in the two-dimensional plane of the image easily and the depth of the probe marker 42 (i.e., its distance from the camera along a third dimensional axis perpendicular to the plane of the image) may be determined based on the apparent size of the marker 42 in the image.

Providing two or more cameras 56 may be advantageous to reduce the likelihood of the surgeon's hands or body from preventing the camera system 22 from obtaining an unobstructed view of the probe marker 42. In an embodiment where at least two cameras 56 are required to have an unobstructed view of the marker 42, the camera system 22 preferably includes 3 or more cameras 56.

Instead of incorporating cameras, the tracking system 22 could alternatively incorporate other types of tracking system sensor that is configured to sense the position of the probe marker and the instrument marker. For example, the tracking system could incorporate one or more of the following exemplary techniques to sense the position of the instrument 16 and of the probe 12: 2D or 3D ultra sound, MRI and CAT scan images, electromagnetic sensing, radio frequency (RF) sensing. Regardless of the technique used, and the technology used, whatever is on the probe and on the instrument that is detected by the tracking system may be considered a probe marker and an instrument marker respectively.

The organ retention device 18 is positionable to retain at least some of the internal body portions 36 in the surgical field 38 from obstructing the surgical instrument 16 when the surgical instrument 16 is being used in the surgical field 38.

Figure 3:
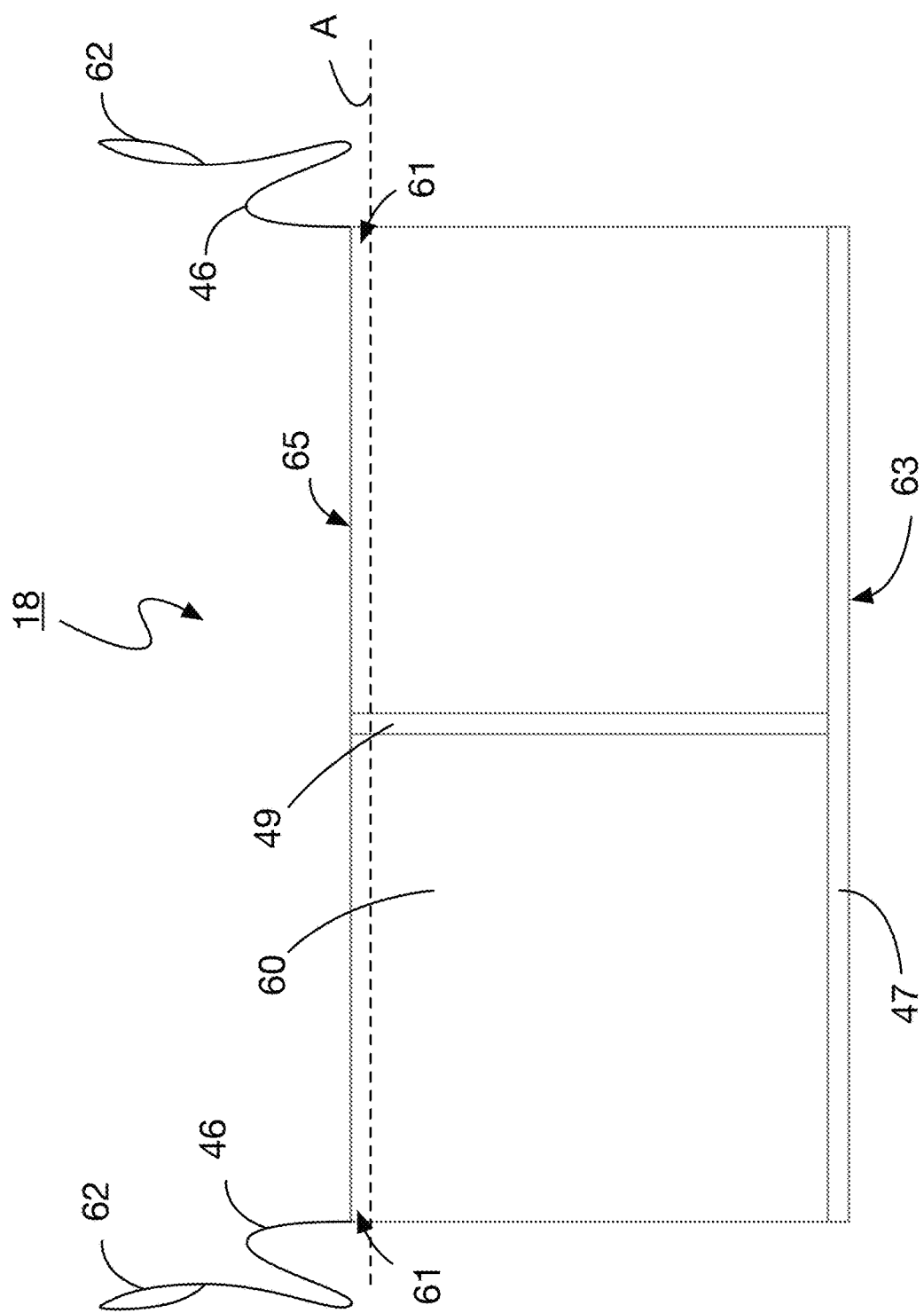
FIG. 3 depicts an organ retention device of the surgical system of FIG. 2.

Referring now to FIGS. 1 to 3, the organ retention device 18 is provided with two biocompatible anchor strings 46 that extend from connection regions 61 of a rectangular netting 60. The anchor strings 46 can form part of the material of the netting or may be secured thereto in some suitable manner. They may be any type of string, thread, strand, wire, etc. that can bear an appropriate level of tension placed thereon to allow the netting 60 to retain one or more organs. The netting 60 is a biologically compatible flexible barrier that is comprised of a layer of material that covers the retained and/or retracted organs. Preferably, the size of the apertures in the netting 60 is sufficiently small to inhibit organs from protruding significantly therethrough. Each connection region 61 is defined by the point(s) at which the corresponding anchor string 46 is connected to the netting 60. Thus, each connection region can be a point or an area. The connection regions 61 are proximate two adjacent vertices along a top peripheral edge 65 of the rectangular netting 60. The two connection regions 61 generally define an axis A that passes through the connection regions 61 and is generally parallel to the top peripheral edge 65. Each of the anchor strings 46 has a loop 62 distal from the netting 60. The anchor strings 46 are configured to be withdrawn from the inside of the body of the patient 26, through the fascia and abdominal wall, and out of an excision hole in the patient 26 via the loops 62, such as via a needle hook. The anchor strings 46 may then be pulled taut via the loops 62, which may then be attached to suitable attachment points on a support frame (not shown). The organ retention device 18 may be made up of one or more individual nets each of which is affixed to internal body portions 36 around the surgical field 38.

The netting 60 has a weighted peripheral structure 47 proximal to or at a bottom peripheral edge 63 of the netting 60 to provide a weighted peripheral region. The weighted peripheral structure 47 provides supplementary weighting via a material in the form of a flexible, biocompatible material such as a silicone bead secured to the weighted peripheral region of the netting 60. That is, additional weight is added proximal to the peripheral edge of the netting 60, such as by thickening the netting 60 at that location, by securing additional material thereto, extending its length beyond that normally required, etc. The weighted peripheral structure 47 acts as an expansion element for the netting 60, causing it to expand generally perpendicularly to the axis A between the connection regions 61 when the connection regions 61 are held apart in tension via the anchor strings 46. That is, to cause the netting 60 to hang downwards through gravity, thereby causing it to expand along two dimensions.

In other embodiments, the weighted peripheral structure can be provided by thickening the netting 60 in the region of the peripheral edge 63, adding material in the region, securing flexible filaments or other weights, such as stainless steel elements, to the region, etc. The weighted peripheral structure can be located in a region above a peripheral edge of the netting 60 where the netting 60 is longer than needed to provide a barrier for retaining the targeted organs.

In addition, a stiffening structure 49 extends along the midline of the netting 60 and generally perpendicularly to the top peripheral edge 65. The stiffening structure 49 is provided via a silicone bead secured to the netting 60 along the midline thereof. In alternative embodiments, the stiffening structure can be provided by thickening the netting 60 in a region, adding material in the region, securing flexible filaments to the region, etc. Where a weighted peripheral structure is employed, such as is the case in the embodiment described above, preferably a stiffening structure that is non-parallel to the axis A is provided to provide rigidity along two dimensions.

The weighted peripheral structure 47 and the stiffening structure 49 provide some rigidity to the netting 60 and resist against the pushing movement of organs deforming in the abdominal cavity. It is also noted that the weighted peripheral structure 47 in this embodiment acts as a stiffening structure as well.

In other embodiments, the stiffening structure can take any shape along the netting 60. Further, more than one stiffening structure can be provided at different regions of the netting 60 or along different axes to further provide resistance to flexure.

All of the netting 60, the weighted peripheral structure 47, the stiffening structure 49, and the anchor strings 46 and loops 62 are made of biocompatible material(s) that are flexible enough to conform to the anatomy the organs against which the organ retaining device 18 is restraining movement, and preferably covers the cross-sectional area of the anatomy of the patient 26. Synthetic materials may be used, and are intended to provide coverage of the organs being retracted and reinforcement to prevent occlusion of the surgical field of view, or worse—inadvertent injury due to obstruction of the surgical site by organ movement. These materials include, but are not limited to, polypropylene, polyethylene, polyethylene terephthalate and/or expanded polytetrafluoroethylene, and may be knitted or woven together, and arranged in flexible planar sheets. Examples of such materials include Ethicon Endosurgery's Prolene polypropylene mesh and Mersilene polyethylene terephthalate mesh, Bard's Marlex mesh constructed from polypropylene. The synthetic or synthetic-bioabsorbable knitted material may also be coated on the side that will face the viscera, with a material or combinations of materials that reduce or prevents the adhesion of bowels or other tissue. Examples of these materials include, but are not limited to sodium hyaluronate and combinations derived thereof; carboxymethylcellulose and polyethyleneglycol; cross-linked omega-3 fatty acid oil; oxidized regenerated cellulose; combinations of monocryl and polydioxanone film, and collagen oxidized films.

Figure 4:
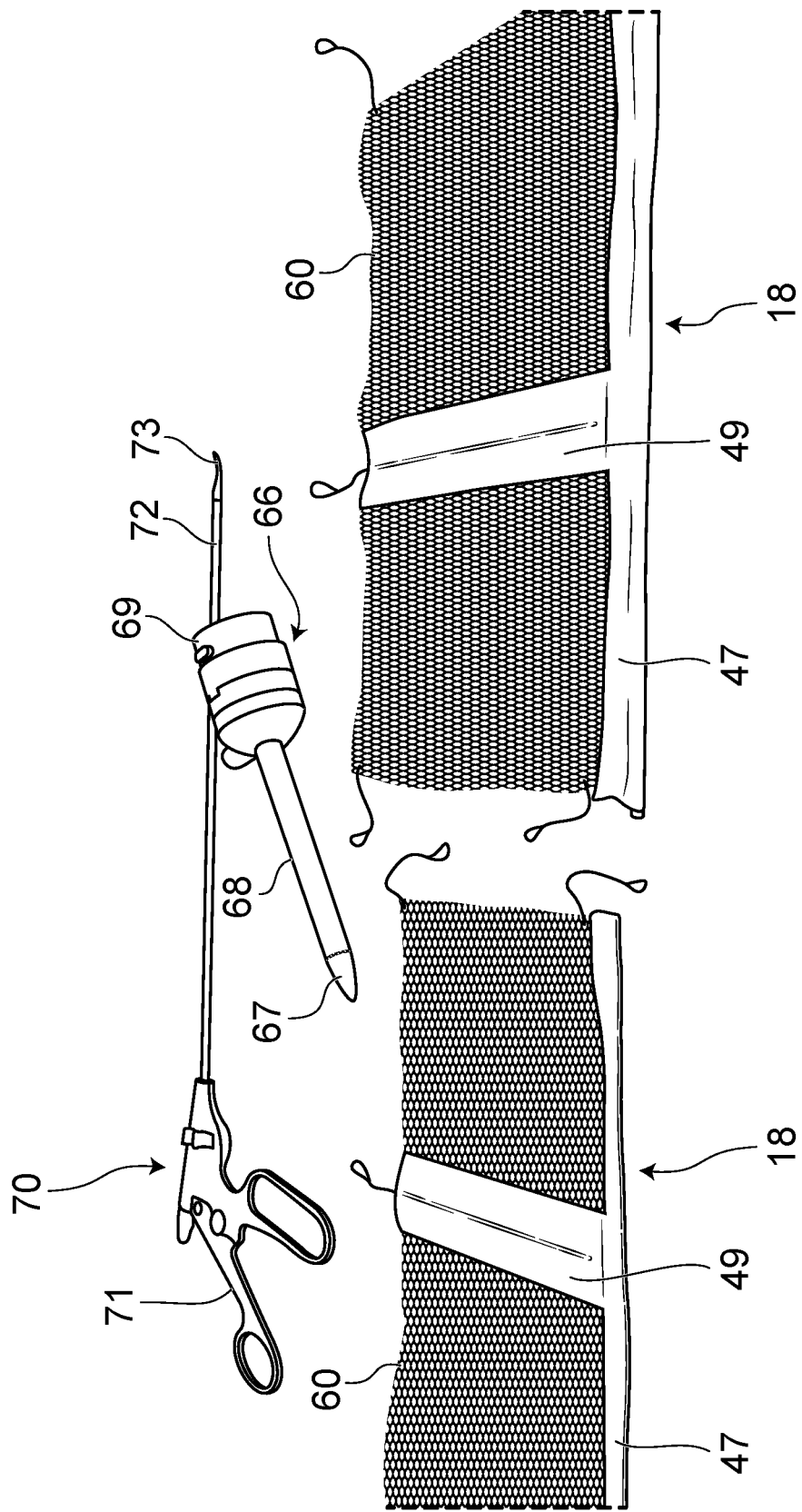
FIG. 4 shows a pair of organ retention devices of FIG. 3, a trocar, and a loop retractor in accordance with an embodiment.

FIG. 4 shows two of the organ retention devices 18 alongside a trocar 66, a medical device that is made up of an obturator 67 (which may be a metal or plastic sharpened or non-bladed tip), a cannula 68 (basically a hollow tube), and a seal 69. The trocar 66 is placed through the abdomen of the patient during laparoscopic surgery, and functions as a portal for the subsequent placement of other instruments, such as graspers, scissors, staplers, etc.

Also shown is an anchor string retraction device in the form of a hook needle tool 70 that is used to retract the loops 62 of the organ retention device 18 out of the patient. The hook needle tool 70 has a grip 71 from which extends an elongated rigid shaft 72 that has a hooked needle point 73. The shaft 72 of the hook needle tool 70 is constructed preferably from a biocompatible, rigid material. Some examples of materials the needle could be constructed from include, but are not limited to 304L stainless steel and other steel alloys; polyhexamethyleneadipamide, (Nylon 66); polyethylene; polycarbonate; polymethyl methacrylate and other acrylic plastics.

In order to deploy the organ retention device 18 in a patient, it is tightly furled and inserted fully through the abdominal wall and into the abdominal cavity via a trocar 66 that has been placed in the patient. Once placed inside the patient, the netting 60 of the organ retention device 18 is unfurled using conventional laparoscopic instruments to expose the loops 62. The weighted peripheral structure 47 provides a marking on the netting 60 to indicate the general orientation in which it should be deployed. As it is desired to have the weighted peripheral structure 47 depend downwardly to expand the netting 60, it is located proximal to the bottom peripheral edge 63 and the top peripheral edge 65 opposite the bottom peripheral edge 63 should be positioned at an upper position where organ retention is required. In other embodiments, other marking can be additionally or alternatively provided, such as via different colored material in a region of the netting, a marker adjacent to or at a peripheral edge to identify it as a top or bottom edge, etc.

The hook needle tool 70 is guided into the abdominal cavity at a desired location for a particular one of the free anchor strings 46 to be anchored, and hooks its loop 62. Upon catching the corresponding loop 62, the surgeon withdraws the hooked needle point 73 back through the entry puncture, pulling the caught loop 62 with it. The friction of the fascia, skin, muscle, fat and other abdominal tissue allows the loop 62 to be pulled through and held in place. This procedure is repeated for each loop 62 that the surgeon wishes to secure, and the netting 60 can be pulled taut or left loose, depending on the patient anatomy and the situated position of organs.

Other types of anchor string retraction devices can be employed to retract the anchor strings 46, such as surgical grabber tools, etc.

The elasticity of the netting 60 allows for flexibility should the bowels or other organs heave against the netting 60, but remains rigid enough to prevent the organs from spilling into the operative site. The fully deployed system urges the organ retention device 18 into a planar shape perpendicular to the abdominal cavity.

Removal of the organ retention device 18 leaves no prosthesis or foreign material in the body. Using conventional laparoscopic surgical tools, the anchor strings 46 are cut, allowing the surgical team to pull the detached loops 62 and portions of the anchor strings 46 out through the body. The netting 60 can be pulled through the largest trocar 66, by grasping the netting 60 by a corner and pulling it directly out of the abdominal cavity through the port. Unlike conventional organ retention devices, an additional person is not required to handle the organ retention device 18, and no trocar 66 is obstructed in any way during the deployment of the organ retention device 18.

Figure 5:
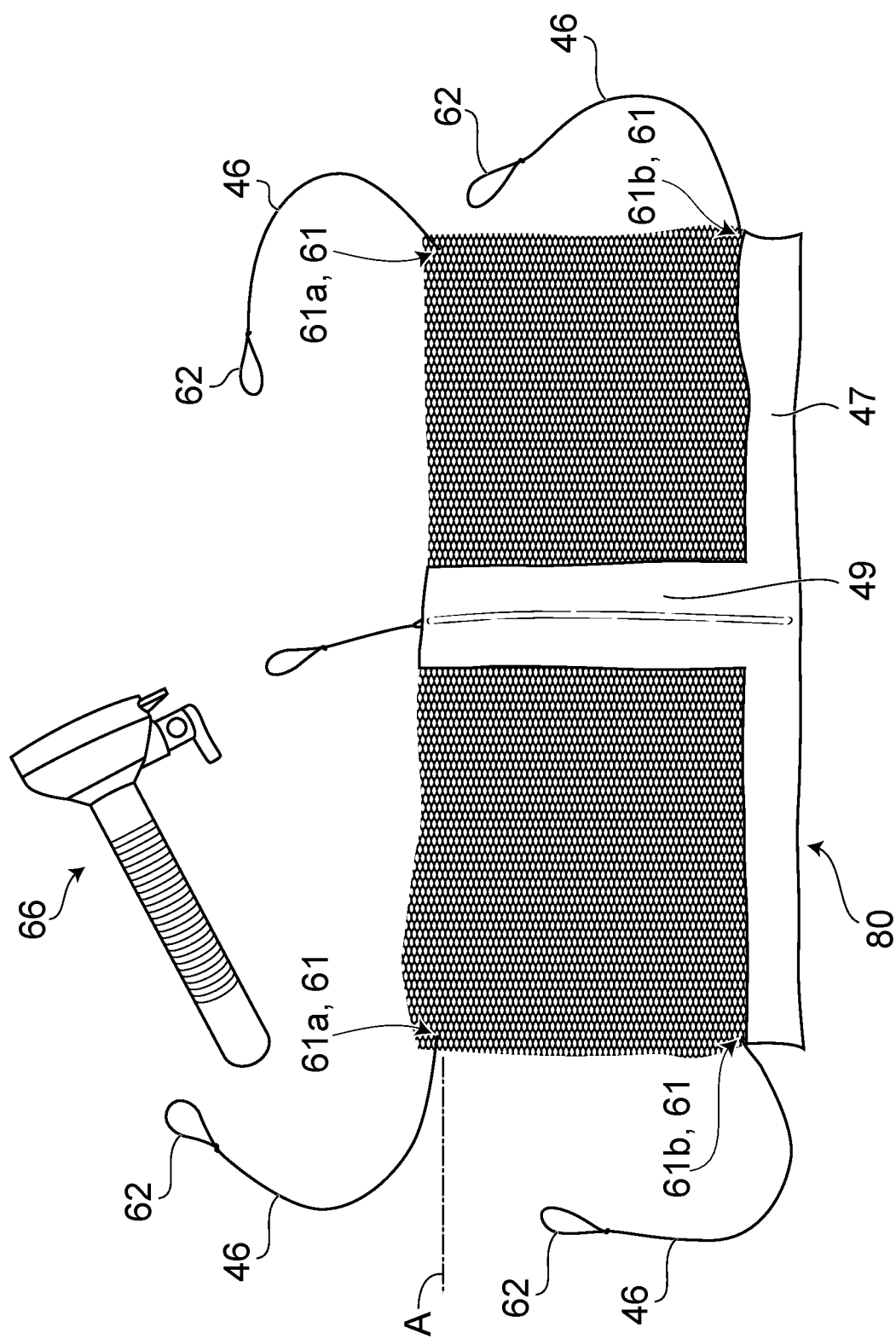
FIG. 5 depicts an organ retention device similar to that of FIGS. 2 to 4 in accordance with another embodiment of the invention.

FIG. 5 shows an organ retention device 80 in accordance with another embodiment. The organ retention device 80 is similar to the organ retention device 18 of FIGS. 2 to 4, except that, in addition to the weighted peripheral structure 47, the organ retention device 80 includes additional expansion elements in the form of additional anchor strings 46 extending from connection regions 61 of the netting 60 and having loops 62 at their ends. In particular, two additional anchor strings 46 extend from connection regions 61b at vertices of the rectangular netting 60 distal from the two connection regions 61a from which anchor strings extended in the embodiment shown in FIGS. 2 to 4, and not being located therebetween so that movement of the connection regions 61b away from the axis causes the netting to expand. The anchor strings 46 extending from the connection points 61b also act to extend the netting 60 away from the axis A defined by the connection regions 61a.

Still further, the organ retention device 80 includes another anchor string 46 that extends from a connection region that is in a central region of the netting 60 delimited by the four connection regions 61a, 61b positioned proximal to the vertices of the netting 60. It may be desirable in some applications such as where the netting 60 is under pressure from the organs or where the surgical tool is being operated close to the netting 60, to control bulging of the netting 60 by applying tension to the central region thereof.

Figure 6:
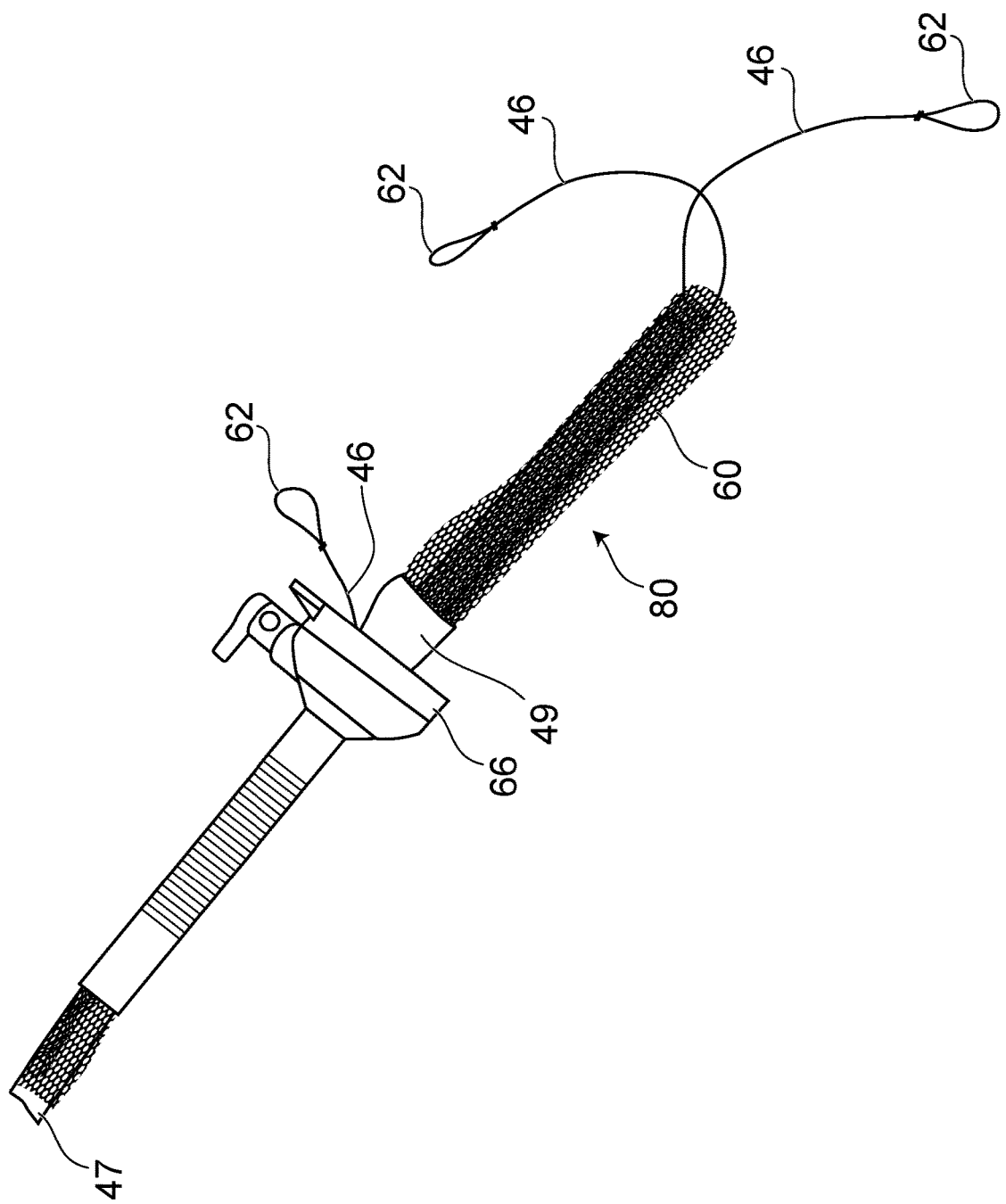
FIG. 6 depicts an organ retention device of FIG. 5 furled up and being passed through a trocar.

FIG. 6 shows the organ retention device 80 furled up and being inserted through a trocar 66. Even with the weighted peripheral structure 47 and the stiffening structure 49, the netting 60 is sufficiently flexible to enable it to be rolled and passed through the trocar 66.

Figure 7:
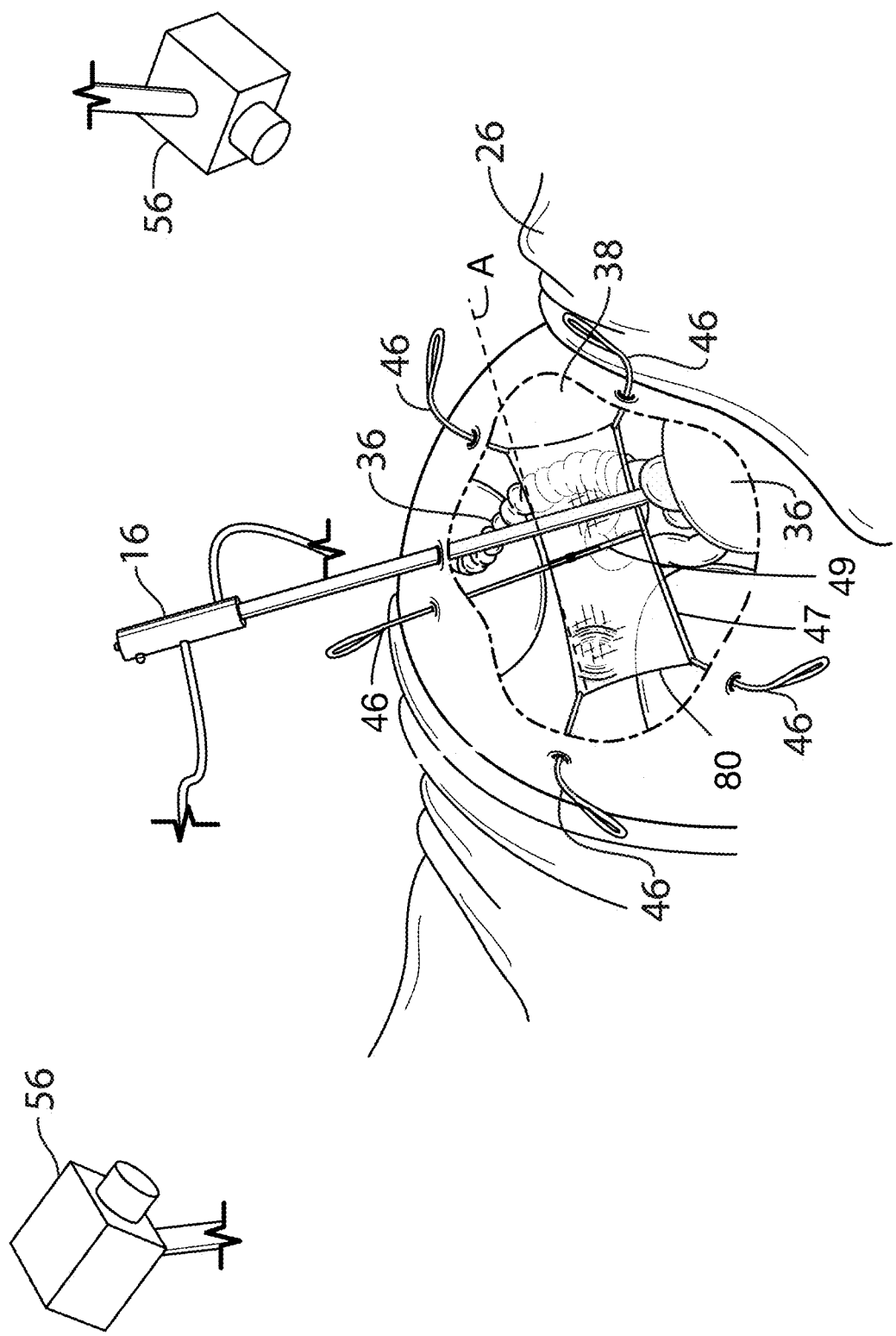
FIG. 7 depicts a netting in accordance with a further embodiment being used as part of a surgical system similar to that of FIG. 1.

FIG. 7 shows the organ retention device 80 deployed within a patient 26. As shown, the anchor strings 46 extend from each of the four vertices of the netting 60 and their loops 62 are retracted using a hook needle tool or another suitable tool for withdrawing the loops 62 out of the body. In addition, the weighted peripheral structure 47 hangs down to extend the netting 60 generally perpendicularly from the axis A extending between the connection regions of the upper two anchor strings 46.

Both the weighted peripheral structure 47 and the stiffening structure 49 act to stiffen the netting 60 to make it resist flexure/bulging as a result of impinging organs.

Further, the anchor string 46 extending from the central region is shown pulled taut.

While, in the above-described embodiments, the flexible barrier is a netting, other types of flexible barriers can be employed. For example, a latex or nylon sheet can be employed to retain one or more organs. The flexible barrier can be non-rectangular and provided in other shapes.

In other embodiments, the anchor strings may, instead of loops, have knots or other features such as widened portions that may be grabbed or, alternatively, may have no such features. Such anchor strings can be employed with surgical grabber tools and the like.

While the above description constitutes a plurality of embodiments of the present invention, it will be appreciated that the present invention is susceptible to further modification and change without departing from the fair meaning of the accompanying claims.

Persons skilled in the art will appreciate that there are yet more alternative implementations and modifications possible, and that the above examples are only illustrations of one or more implementations. The scope, therefore, is only to be limited by the claims appended hereto.

The invention claimed is:

1. An organ retention device, comprising:
    a biologically compatible flexible barrier configured to restrain one or more organs;
    a first anchor string extending from a first connection region of the flexible barrier;
    a second anchor string extending from a second connection region of the flexible barrier, a top peripheral region of the flexible barrier extending between the first connection region and the second connection region; and
    at least one expansion element coupled to the flexible barrier at a weighted peripheral region spaced from the top peripheral region to expand the flexible barrier generally perpendicularly to the top peripheral region, wherein the at least one expansion element comprises supplementary weighting along the weighted peripheral region of the flexible barrier and spaced from the top peripheral region to cause the weighted peripheral region to hang down from the top peripheral region when the first connection region and the second connection region are held apart in tension.

2. The organ retention device according to claim 1, wherein the flexible barrier comprises a netting.

3. The organ retention device according to claim 2, wherein the first anchor string has a first loop distal from the flexible barrier and wherein the second anchor string has a second loop distal from the flexible barrier.

4. An organ retention system for laparoscopic surgery, comprising:
    the organ retention device according to claim 3; and
    an anchor string retraction device having a sharp distal end configured to enter an abdominal cavity by puncturing the abdominal wall of a patient, and a hook proximate to the sharp distal end configured to catch one of the loops of the organ retention device and retract the captured loop through viscera of the abdominal wall to anchor the corresponding connection region of the flexible barrier.

5. The organ retention device according to claim 2, further comprising a stiffening structure of the flexible barrier reducing the flexibility of the netting.

6. The organ retention device according to claim 5, wherein the stiffening structure extends at least partially between the top peripheral region and the weighted peripheral region.

7. The organ retention device according to claim 6, wherein the stiffening structure comprises silicone beading secured to the netting.

8. The organ retention device according to claim 7, wherein the silicone beading is applied along a line that is generally non-parallel to the top peripheral region when the first connection region and the second connection region are held apart in tension.

9. The organ retention device according to claim 2, wherein the at least one expansion element comprises:
    a third anchor string extending from a third connection region of the flexible barrier; and
    a fourth anchor string extending from a fourth connection region of the flexible barrier.

10. The organ retention device according to claim 9, further comprising:
    a fifth anchor string extending from a fifth connection region of the flexible barrier, the fifth connection region being positioned within a central region of the flexible barrier delimited by the first, second, third, and fourth connection regions.

11. The organ retention device according to claim 10, wherein the third anchor string has a third loop distal from the flexible barrier, wherein the fourth anchor string has a fourth loop distal from the flexible barrier, and wherein the fifth anchor string has a fifth loop distal from the flexible barrier.

12. The organ retention device according to claim 10, wherein the flexible barrier is generally rectangular, and wherein each of the first, second, third, and fourth connection regions are proximate to a separate vertex of the flexible barrier.

13. The organ retention device according to claim 2, further comprising marking on the netting indicating orientation.

14. The organ retention device according to claim 13, wherein the marking comprises silicone beading on the netting.

15. The organ retention device according to claim 1, wherein the supplementary weighting comprises material secured to the weighted peripheral region.

16. The organ retention device according to claim 15, wherein the weighting material comprises silicone.

17. The organ retention device according to claim 16, wherein the supplementary weighting comprises silicone beading secured along the weighted peripheral region of the flexible barrier.

* * * * *